(12) United States Patent
Ludin et al.

(10) Patent No.: US 6,495,336 B1
(45) Date of Patent: Dec. 17, 2002

(54) OLIGOPEPTIDE DERIVATIVES FOR THE ELECTROCHEMICAL MEASUREMENT OF PROTEASE ACTIVITY

(75) Inventors: Christian Ludin, Reinach (CH); Peter Wikstroem, Gipf-Oberfrick (CH); Lars G. Svendsen, Reinach (CH); Andreas Schulze, Aesch (CH)

(73) Assignee: Pentapharm AG (CH)

( * ) Notice: Subject to any disclaimer, the term of this patent is extended or adjusted under 35 U.S.C. 154(b) by 0 days.

(21) Appl. No.: 09/914,259

(22) PCT Filed: Feb. 23, 1999

(86) PCT No.: PCT/CH99/00082

§ 371 (c)(1),
(2), (4) Date: Nov. 21, 2001

(87) PCT Pub. No.: WO00/50446

PCT Pub. Date: Aug. 31, 2000

(51) Int. Cl.[7] .................. C07K 5/083; C07K 5/087; C07K 5/103; C07K 5/107; G01N 33/68
(52) U.S. Cl. .................. 435/13; 205/777.5; 435/23; 530/331; 530/345
(58) Field of Search ................ 530/331, 345; 435/13, 23, 24; 205/777.5, 778

(56) References Cited

U.S. PATENT DOCUMENTS

| 4,304,853 | A |   | 12/1981 | Jozefonvicz et al. ..... 205/777.5 |
|---|---|---|---|---|
| 4,440,678 | A |   | 4/1984 | Svendsen .................... 530/331 |
| 4,505,852 | A |   | 3/1985 | Rasnick et al. ............. 530/329 |
| 4,584,398 | A |   | 4/1986 | Kuroiwa et al. ............ 562/439 |
| 5,059,525 | A |   | 10/1991 | Boehringer .................. 435/13 |
| 5,223,404 | A | * | 6/1993 | Suido et al. ................. 435/24 |
| 5,225,532 | A | * | 7/1993 | Quentin et al. ............. 530/331 |

FOREIGN PATENT DOCUMENTS

| AU | 564556 B | 8/1987 |
| DE | 34 28 543 A | 2/1986 |
| EP | 0 018 002 A | 10/1980 |
| EP | 0 034 122 A | 8/1981 |
| EP | 0 152 872 A | 8/1985 |
| EP | 0 182 373 A | 5/1986 |

* cited by examiner

*Primary Examiner*—Jeffrey E. Russel
(74) *Attorney, Agent, or Firm*—Pennie & Edmonds LLP

(57) ABSTRACT

The invention relates to oligopeptide derivatives whose C-terminal amino acid is arginine which is linked to the remainder of an electroactive aniline or aminoquinoline derivative by an amide bond. The oligopeptide derivatives are split by enzymes of the class of peptide hydrolases, especially proteinases and their inhibitors, of the coagulation system, the fibrinolytic system and the complement system. These oligopeptide derivatives serve as substrates for quantitatively determining such enzymes, especially thrombin, in complex sample liquids, especially capillary blood. This determination is carried out by measuring the increase in the water-soluble amperogenic aniline or aminoquinoline compound. The oligopeptide derivatives and their salts can be produced according to usual methods in peptide chemistry.

18 Claims, 12 Drawing Sheets

OLIGOPEPTIDE DERIVATIVES FOR THE ELECTROCHEMICAL MEASUREMENT OF PROTEASE ACTIVITY

The present invention relates to oligopeptide derivatives of the formula (I)

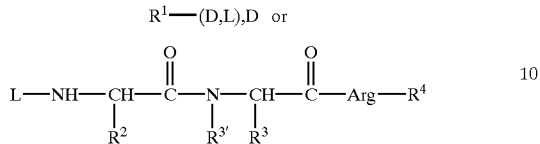

in which
$R^1$ is
(a) a hydrogen atom, a $C_{2-8}$-alkanoyl group optionally having an amino group in the ω position, a phenyl-$C_{2-4}$-alkanoyl group whose phenyl radical is optionally substituted in the p position by an amino group; or
(b) a cyclohexylcarbonyl group which is optionally substituted in the 4 position by an aminomethyl radical, a benzoyl group which is optionally substituted in the o or p position by methyl, amino or halogen, a $C_{1-8}$-alkoxycarbonyl group, a benzyloxycarbonyl group which is optionally substituted in the p position by methoxy, methyl or chlorine; or
(c) a radical of the formula —$SO_2$—$R^5$ where $R^5$ can be a $C_{1-6}$-alkyl radical, an optionally substituted aryl or heteroaryl radical or a radical of a bicyclic terpene derivative; or
(d) a group of the formula —CO—CH($R^6$)—NH—$R^7$, where $R^6$ is hydrogen, a $C_{1-6}$-alkyl radical, a 1- or 2-hydroxyethyl radical, a methylmercaptoethyl radical, an aminobutyl radical, a guanidinopropyl radical, a carboxy-$C_{1-4}$-alkyl radical, a carboxamido-$C_{1-4}$-alkyl radical, a phenyl-$C_{1-4}$-alkyl radical whose phenyl radical is optionally substituted by OH, halogen, $C_{1-4}$-alkyl or methoxy, or a cyclohexyl or cyclohexylmethyl radical whose ring is optionally substituted by OH, halogen, $C_{1-4}$-alkyl or methoxy, or a nitrogen-containing heteroaryl-$C_{1-4}$-alkyl radical with 3 to 8 carbon atoms in the heterocyclic system, where the group —CO—CH($R^6$)—NH—$R^7$ may be racemic or have the D or L configuration, and $R^7$ can be a group of type (a), (b) or (c); or
(e) a group of the formula

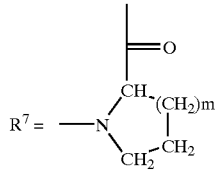

where $R^7$ has the above meaning, m can be 1 or 2, and one of the methylene groups can be substituted by hydroxyl, carboxyl, $C_{1-4}$-alkyl or aryl-$C_{1-4}$-alkyl;
$R^2$ is hydrogen, $C_{1-6}$-alkyl, $C_{1-2}$-hydroxyalkyl, $C_{1-4}$-alkoxy-$C_{1-6}$-alkyl, benzyloxy-$C_{1-2}$-alkyl, an ω-carboxy-$C_{1-3}$-alkyl radical, an ω-$C_{1-4}$-alkoxycarbonyl-$C_{1-3}$-alkyl radical, an ω-benzyloxycarbonyl-$C_{1-3}$-alkyl radical or a cyclohexyl, cyclohexylmethyl, 4-hydroxycyclohexylmethyl, phenyl, benzyl, 4-hyroxybenzyl or imidazolyl-4-methyl radical;

$R^3$ is
(a) hydrogen or $C_{1-4}$-alkyl and $R^{3'}$ is hydrogen; or
(b) together with $R^{3'}$ a tri- or tetramethylene group, where one of the methylene groups can be substituted by hydroxyl, carboxyl, $C_{1-4}$-alkyl or aryl-$C_{1-4}$-alkyl; and $R^4$ is
(a) an aniline residue of the formula

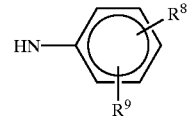

where $R^8$ can be hydroxyl or amino and $R^9$ can be hydrogen, halogen, amino, nitro, $C_{1-4}$-alkyl, $C_{1-4}$-alkoxy or $C_{1-4}$-alkanoyl; or
(b) a quinoline residue of the formula

where one of $R^{10}$, $R^{11}$ and $R^{12}$ is an —NH group via which the quinoline residue is linked to the Arg residue, a second one can be hydroxyl or amino, and the third one can be hydrogen, hydroxyl or amino;

and the salts thereof.

These oligopeptide derivatives and the salts are novel. They are cleaved by enzymes of the peptide hydrolase enzyme class (E.C. 3.4.), in particular proteinases (E.C. 3.4.21–99) and inhibitors thereof, of the blood coagulation system, of the fibrinolytic system and of complement, in particular of thrombin. They thus serve as substrates for the quantitative and qualitative determination of the abovementioned enzymes, in particular thrombin, in complex sample liquids, in particular capillary blood.

The present invention relates to novel oligopeptide derivatives of the formula (I) and salts thereof, to the preparation of these oligopeptide derivatives and salts, and to a method for the quantitative determination of a protease or antiprotease, in particular of the blood coagulation system, of the fibrinolytic system or of complement, in particular thrombin, which is carried out by means of the novel oligopeptide derivatives or salts thereof.

The term "alkyl" used in this description designates, on its own or in combinations such as "hydroxyalkyl" or "benzyloxyalkyl", straight-chain or branched saturated hydrocarbon radicals such as methyl, ethyl, n-propyl, isopropyl, n-butyl, isobutyl, sec-butyl, tert-butyl and the like. The term "alkoxy" designates an alkyl radical within the meaning of the above definition of "alkyl", which is linked via an oxygen bridge. The term "alkanoyl" designates the acyl radical of an alkylcarboxylic acid which may be straight-chain or branched, such as acetyl, propionyl and the like. The term "aryl" designates the radical of an aromatic hydrocarbon and comprises radicals such as phenyl, naphthyl and the like. The term "heteroaryl" designates the radical of an aromatic heterocyclic system such as imidazolyl, indolyl, quinolinyl, isoquinolinyl and the like.

If $R^1$ in formula (I) is a radical of the formula —$SO_2R^5$, then $R^5$ can be, for example, methyl, isopropyl, phenyl, tert-butylphenyl, 4-methylphenyl, 2,4,6-trimethylphenyl, 2,4,6-triisopropylphenyl, 4-methoxy-2,3,6-trimethylphenyl, anthraquinoyl, 1- or 2-naphtyl, quinolyl or isoquinolyl or a radical derived from camphor. If, in formula (I), $R^1$ is a group of the formula —CO—CH($R^6$)—NH—$R^7$ and $R^6$ is heteroarylalkyl, then $R^6$ can be, for example, imidazolylmethyl or indolylmethyl.

If the N-terminal amino acid in the molecule carries a protective group, then this protective group is expediently tert-butoxycarbonyl ("Boc"), p-toluenesulfonyl ("Tos"), tert-butylphenylsulfonyl ("t-Bups"), methylsulfonyl ("Mes"), naphthylsulfonyl ("Naps"), benzoyl ("Bzo"), benzyloxycarbonyl ("Z"), isopropylsulfonyl or camphorsulfonyl.

If $R^4$ is an aniline residue, then expediently $R^8$ is hydroxyl in the o- or p position and $R^9$ is halogen in the m position or $R^8$ is hydroxyl in the o, m or p position and $R^9$ is nitro or $C_{1-4}$-alkanoyl in the m or p position. The radical $R^4$ is preferably derived from 2-amino-4-nitrophenol, 4-amino-2-nitrophenol, 4-amino-3-nitrophenol, 2-amino-5-nitrophenol, 2,4-diaminotoluene, 2,4-diaminophenol, 4-amino-m-cresol, 2,5-diaminoanisole, 4-nitro-o-phenylenediamine, 2-amino-4-chlorophenol, 4-amino-2-chlorophenol, 4-amino-3-chlorophenol, 4-fluoro-2-aminophenol, 2-fluoro-4-aminophenol, 5-fluoro-2-aminophenol, 5-amino-8-hydroxyquinoline or 2-amino-8-hydroxyquinoline.

The oligopeptide derivatives of the formula (I) contain L-arginine ("Arg") as C-terminal amino acid. Further amino acids which may be present in the molecule are, for example, 2-aminobutyric acid, alanine, 3-cyclohexylalanine, 2-cyclohexylglycine, phenylalanine, pipecolic acid, proline and valine, it being possibe for these amino acids to be in the L, D or DL form, and glycine; preference is given in this connection to L-alanine ("Ala"), L-2-aminobutyric acid ("Abu"), D-3-cyclohexylalanine ("D-Cha"), D-2-cyclohexylglycine ("D-Chg"), glycine ("Gly") and L-proline ("Pro").

Representative examples of oligopeptide derivatives of the formula (I) are:

H-(D)-Chg-Gly-Arg 3-chloro-4-hydroxyanilide;
Boc-(D)-Chg-Gly-Arg 3-chloro-4-hydroxyanilide;
Tos-(D)-Chg-Gly-Arg 3-chloro-4-hydroxyanilide;
t-Bups-(D)-Chg-Gly-Arg 3-chloro-4-hydroxyanilide;
Mes-(D)-Chg-Gly-Arg 3-chloro-4-hydroxyanilide;
Naps-2-(D)-Chg-Gly-Arg 3-chloro-4-hydroxyanilide;
Z-(D)-Chg-Gly-Arg 3-chloro-4-hydroxyanilide;
H-(D)-Cha-Gly-Arg 3-chloro-4-hydroxyanilide;
Boc-(D)-Cha-Gly-Arg 3-chloro-4-hydroxyanilide;
H-Gly-Pro-Arg 3-chloro-4-hydroxyanilide;
Boc-Gly-Pro-Arg 3-chloro-4-hydroxyanilide;
Tos-Gly-Pro-Arg 3-chloro-4-hydroxyanilide;
t-Bups-Gly-Pro-Arg 3-chloro-4-hydroxyanilide;
Mes-Gly-Pro-Arg 3-chloro-4-hydroxyanilide;
isopropylsulfonyl-Gly-Pro-Arg 3-chloro-4-hydroxyanilide;
Naps-2-Gly-Pro-Arg 3-chloro-4-hydroxyanilide;
(−)-camphorsulfonyl-Gly-Pro-Arg 3-chloro-4-hydroxyanilide;
H-(D)-Cha-Pro-Arg 3-chloro-4-hydroxyanilide;
Boc-(D)-Cha-Pro-Arg 3-chloro-4-hydroxyanilide;
H-(D)-Cha-Ala-Arg 3-chloro-4-hydroxyanilide;
Boc-(D)-Cha-Ala-Arg 3-chloro-4-hydroxyanilide;
Boc-(D)-Cha-Abu-Arg 3-chloro-4-hydroxyanilide;
Z-Gly-Pro-Arg 2-chloro-4-hydroxyanilide;
Z-Gly-Pro-Arg 5-chloro-2-hydroxyanilide;
Z-Gly-Pro- Arg 8-hydroxyquinolin-5-ylamide;
Boc-(D)-Chg-Gly-Pro-Arg 3-chloro-4-hydroxyanilide;
H-(D)-Chg-Gly-Pro-Arg 3-chloro-4-hydroxyanilide; and
t-Bups-(D)-Chg-Gly-Pro-Arg 3-chloro-4-hydroxyanilide.

In the bloodstream numerous proteinases reach their site of action in the body. This underlines the importance of knowledge of the enzymic activity for understanding a wide variety of pathological states. Derangements of the balance between enzyme and inhibitor are responsible for the onset of an illness. It is therefore of inestimable value to be able to determine the enzymic activity present.

Blood or plasma are, however, not easy to handle as analysis media because of their properties (viscosity, absorption of visible light). In most cases, enzyme assays are carried out by photometric methods. There are limits to this especially in the case of blood, plasma or serum.

Photometric detection methods usually require clear sample solutions because the chromogenic properties of the synthetic substrates used and the chromophores thereof otherwise cannot have an effect. This often gives rise to preceding purification steps in order to obtain a measurable solution (compare DE 3616496 A1 and DE 19549117 A1).

Measurements of the enzymes of the blood coagulation system are, for example, d desired and carried out in patients with heart valve replacement or after myocardial infarctions. Patients of these types are subjected to a therapy with oral anticoagulants. The intention therewith is to prevent further thrombo-embolic events. For this purpose, the patients are treated at regular intervals with medicaments from the class of coumarin derivatives. However, this therapy requires monitoring for optimal dosage. The parameter of choice in order r to be able to derive an optimal dosage is determination of the Quick prothrombin time (PT).

The oligopeptide derivatives according g to the present invention make it possible to determine the prothrombin time using a substrate which generates an electrochemical signal. It is additionally possible to generate a sufficiently good signal from capillary blood.

European patent EP 0018002 B1 describes an electrochemical method for the determination of proteases of the blood coagulation systems, in particular of antithrombin, in citrated plasma using amperogenic substrates. Unfortunately, inaccuracies of measurement are possible in this elegant method for direct determination of thrombin or trypsin, because the addition of a solubilizer (DMSO) to the reaction medium is necessary to keep the amperogenic substrate dissolved in the reaction medium (J. M. Nigretto et al., Thrombosis Research 20, 299–306, 1980; Thrombosis Research 22, 303–308). The addition of a cosolvent may lead to an inaccuracy in the measurement of thrombin for practical use, for example screenings in the complex system of blood plasma or blood, for example through inducing coagulation, compromising an enzyme in the cascade, local substrate precipitation effects or the like.

The oligopeptide derivatives of the present invention now make possible a novel, direct amperogenic thrombin determination method which is better adapted to practice than previously disclosed determination methods. In this method, the increase in a water-soluble amperogenic compound resulting from the hydrolysis of the substrate by the enzyme is measured. This involves cleavage of a peptide residue whose C-terminal peptide residue is L-arginine, and of an electroactive residue which is connected by an amide linkage to the L-arginine, by the enzyme. The electroactive residue is then electrochemically oxidized or reduced, the change in the current is measured, and the latter is proportional to the concentration of the amperogenic residue formed during the enzymatic hydrolysis.

The method of the invention makes quantitative determination of a protease of antiprotease possible, in particular of the blood coagulation system, of the fibrinolytic system or of complement, in particular thrombin; it is characterized in that the enzyme is contacted in an aqueous or organic medium with an oligopeptide derivative of the formula (I) or a salt thereof, and the electroactive amine of the formula H—$R^4$, in which $R^4$ has the above meaning, which is cleaved off by the enzyme to be determined and which can be electrochemically oxidized or reduced, is determined by amperometry.

The amperometry is expediently carried out using an apparatus with a potentiostat and a measuring cell with two or three electrodes, a measuring electrode made of steel or a noble metal, such as platinum or gold, a reference electrode and/or an auxiliary electrode, where the oligopeptide derivative of the formula (I) or salt thereof and possible water-soluble additions such as $Ca^{++}$ salts, phospholipids or thromboplastin reagents is or are applied to the electrodes.

The change in the concentration of the electroactive amine of the formula $R^4$—H in which $R^4$ has the above meaning can be determined in the measuring cell through the measured oxidation or reduction current.

In a preferred embodiment of the determination method of the invention, a direct adhesion of these water-soluble substrates and of possible water-soluble additions such as, for example $Ca^{++}$, phospholipids, Innovin® (from DADE-Behring) on a conducting surface made of steel or noble metal is possible, with the necessary electrodes being separated by an isolated bar. After addition of media which contain thrombin or which has been generated beforehand, for example in the blood or blood plasma with activators, for example $Ca^{++}$, phospholipids, thromboplastin reagents or the like, the substrate is completely dissolved so that, through the liberation of the amperogenic amino compound, a direct determination of the current, proportional to the concentration of the electroactive amino compound, and thus the determination of the enzyme concentration in the medium, is possible.

It is surprising that, in contrast to EP 0 565 665, a mixture of 0–35% of L-α-phosphatidylcholine (PC) and 65–100% of L-α-phosphatidyl-L-serine (PS) is preferably used as phospholipids.

A particularly preferred mixing ratio of the phospholipids PC:PS is 65 to 75% PS and 25 to 35% PC.

The determination method of the invention can be used to determine thrombin in whole blood: whole blood is applied directly, without removal of blood cells and without removal of other constituents of blood, onto an electrode to which an oligopeptide derivative of the formula (I) or a salt thereof and possible water-soluble additions are adhering.

The substrate of the determination method of the invention, namely an oligopeptide derivative of the formula (I), consists of an oligopeptide residue to which the residue of a water-soluble aromatic or heteroaromatic amine is bonded. These residues of aromatic or heteroaromatic amines have additional functional groups such as, for example, hydroxyl groups or halogen atoms, which advantageously contribute to a lower electrochemical potential and crucially determine the solubility of the substrate in aqueous medium.

The oligopeptide derivatives of the formula (I) and salts thereof can be prepared according to the invention by using methods customary in peptide chemistry (general methods of M. Bodanszky "The Practice of Peptide Synthesis" Springer Verlag, 2nd edition 1994) to link an amine of the formula H—$R^4$ in which $R^4$ has the above meaning to the carboxyl group of arginine, whose amino group is protected or already has the appropriately protected residue of the peptide part of the desired product or a part thereof, and whose arginine group is protected, and, if necessary, the peptide part of the desired product is assembled completely, after which, if desired, the remaining protective group(s) is/are cleaved off and, if desired, a free amino group is acylated and/or, if desired, a resulting oligopeptide derivative of the above formula (I) is converted into an acid addition salt and/or a resulting acid addition salt of such an oligopeptide derivative is converted into a free oligopeptide derivative or into another salt.

The procedure can be such, for example, that the electroactive amino group is attached to the carboxyl group of the C-terminal arginine, its amino group being protected by a protective group, for example a benzyloxycarbonyl or tert-butyloxycarbonyl group, and the guanidino group of arginine being protected by protonization, for example with HCl or p-toluenesulfonic acid. The C-terminal electroactive amino group likewise serves as protective group during the stepwise assembly of the peptide chain. The other protective groups can be cleaved off selectively as required in order to attach the other amino acid residues, until the desired chain length is completely assembled. Finally, the remaining protective groups can be cleaved off completely without involving the electroactive amino group.

Oligopeptide derivatives with free N-terminal amino group can be acylated, for example with t-butylphenylsulfonyl chloride, tosyl chloride, acetyl chloride, butyl chloride, octanoyl chloride, benzoyl chloride, p-methylbenzoyl chloride, 2-chlorobenzoyl chloride, methylsulfonyl chloride, n-butylsulfonyl chloride, t-butylsulfonyl chloride, isopropylsulfonyl chloride, phenylsulfonyl chloride, 1- or 2-naphthylsulfonyl chloride, (+)- or (–)-camphorsulfonyl chloride or with malonyl chloride.

Preferred salts of oligopeptide derivatives of the formula (I) are those in which the strongly basic guanidino group of arginine is stabilized by protonization with HCl, HBr, $H_2SO_4$ or $H_3PO_4$ or with formic, acetic, propionic, phthalic, citric, oxalic, tartaric, benzoic, lactic, trichloroacetic or trifluoroacetic acid, in particular with HCl, acetic acid or trifluoroacetic acid.

In the determination method of the invention, the enzyme to be determined cleaves the bond between the carboxy-terminal amino acid arginine and the water-soluble aromatic or heterocyclic amine. The measurement method comprises electrochemical determination of the amount of liberated amine ("electroactive species"). This electrochemcial determination method is suitable for determining proteases of the blood coagulation systems, in particular thrombin.

The substrate of this determination method consists, for example, of tosyl-glycyl-prolyl-arginyl-3-chloro-4-hydroxyanilide monoacetate salt, in which case the following enzymatic reaction occurs:

Substrate: Tos-Gly-Pro-Arg 3-chloro-4-hydroxyanilide×AcOH+ enzyme↓thrombin

Product: Tos-Gly-Pro-Arg-OH+4-amino-2-chlorophenol

The particular advantage of the determination method of the invention is that the substrates are dissolved homogeneously in any aqueous reaction medium without addition of solubilizers such as, for example, DMSO. It is therefore possible with this electrochemical determination method to determine the enzyme concentration in the reaction medium with high measurement accuracy.

BRIEF DESCRIPTION OF THE DRAWINGS

An expedient embodiment of the determination method of the invention is explained in detail below with reference to the appended drawings.

These show.

I. Apparatuses Used

1) A Tacusell PGP201 potentiostat, software VM1, which maintains a constant potential difference between the measuring electrode and reference electrode, is used. The measuring cell used is a glass beaker with a capacity of 25 ml or 1 ml, which can receive the 3 electrodes.

2) A platinum wire with a surface area of 34 mm$^2$ or 3 mm$^2$ is used as measuring electrode.

3) A calomel electrode (SCE) is used as reference electrode at which the potentials are measured.

4) The auxiliary electrode consists of platinum wire and serves to ensure passage of the current.

5) The measured solution is stirred by a magnetic stirrer for homogenization.

II. Recording the Cyclic Voltammograms

1) Firstly the background current of the buffer is measured in a 25 ml glass beaker with a cycle from −30 to 600 mV at 500 mV/min. A measurement cycle can take place when the basic current affords sufficient accuracy. The basic current is subtracted from the measurement during the hydrolysis of a substrate or the recording of a profile of an electroactive compound.

2) Evaluation of the results: the currents recorded in the linearity range are, after subtraction of the basic current at the relevant potential, proportional to the concentration of the electroactive species during the hydrolysis. The liberated electroactive species, which is cleaved off by the substrate, is likewise proportional to the enzyme concentration employed.

Figure 1:
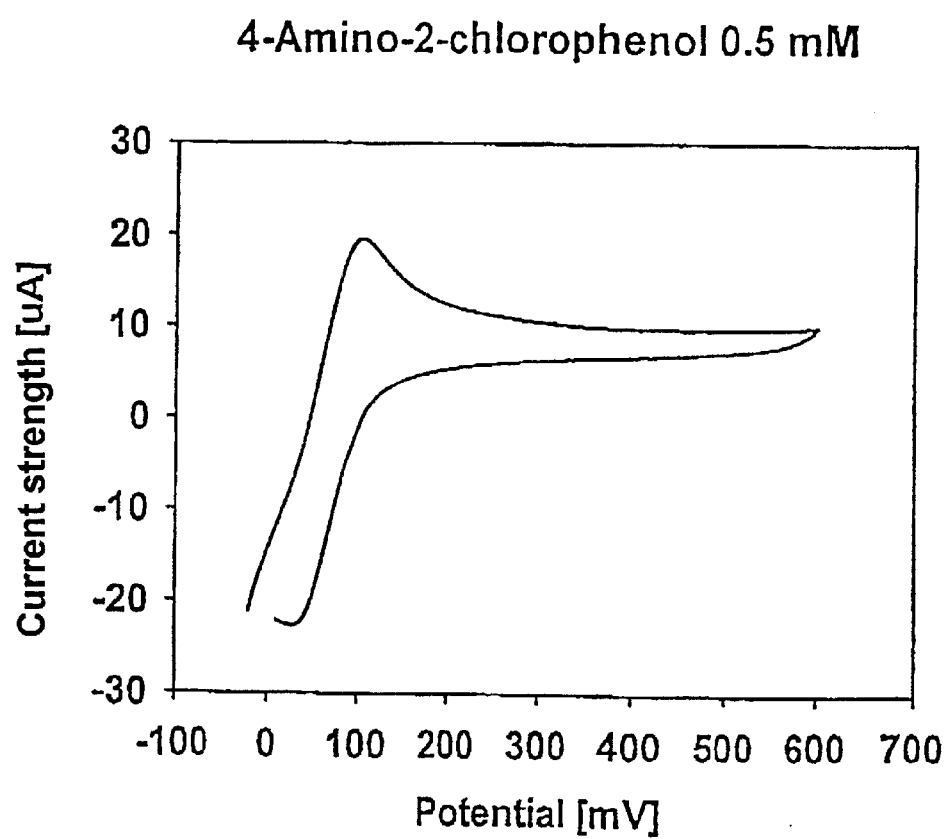
FIG. 1 a voltammogram of 4-amino-2-chlorophenol.
Figure 2:
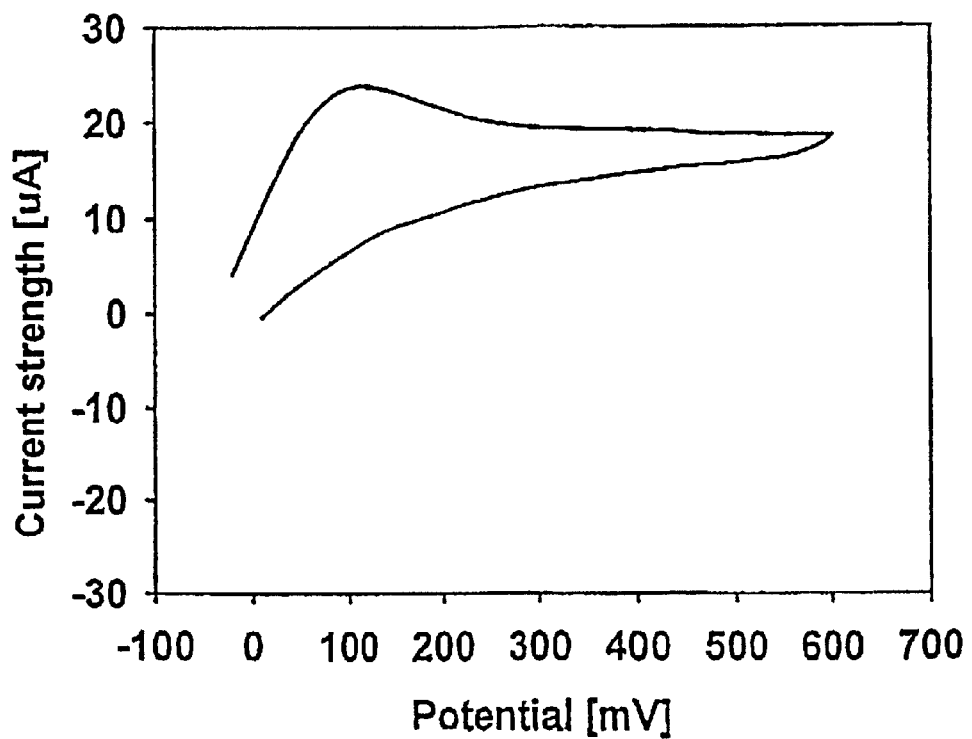
FIG. 2 a voltammogram of 5-amino-8-hydroxyquinoline.

3) A platinum electrode is used to record the cyclic voltammograms at concentrations of 0.25 mmol, 0.5 mmol and 1.0 mmol. HEPES, 50 mmol at pH 7.4, is used as buffer. FIGS. 1 and 2 show typical cyclic reversible plots for 4-amino-2-chlorophenol and 5-amino-8-hydroxyquinoline: recorded from −30 to 600 mV at 500 mV/min. These amperogenic substances preferably show a linear dependence of the current strength on the concentration at low potential in the region of 300 mV, with a high current strength. The system is in equilibrium in this case. A higher voltage of >400 mV is undesired because of interference with possible constituents in the blood, for example paracetamol.

Figure 3:
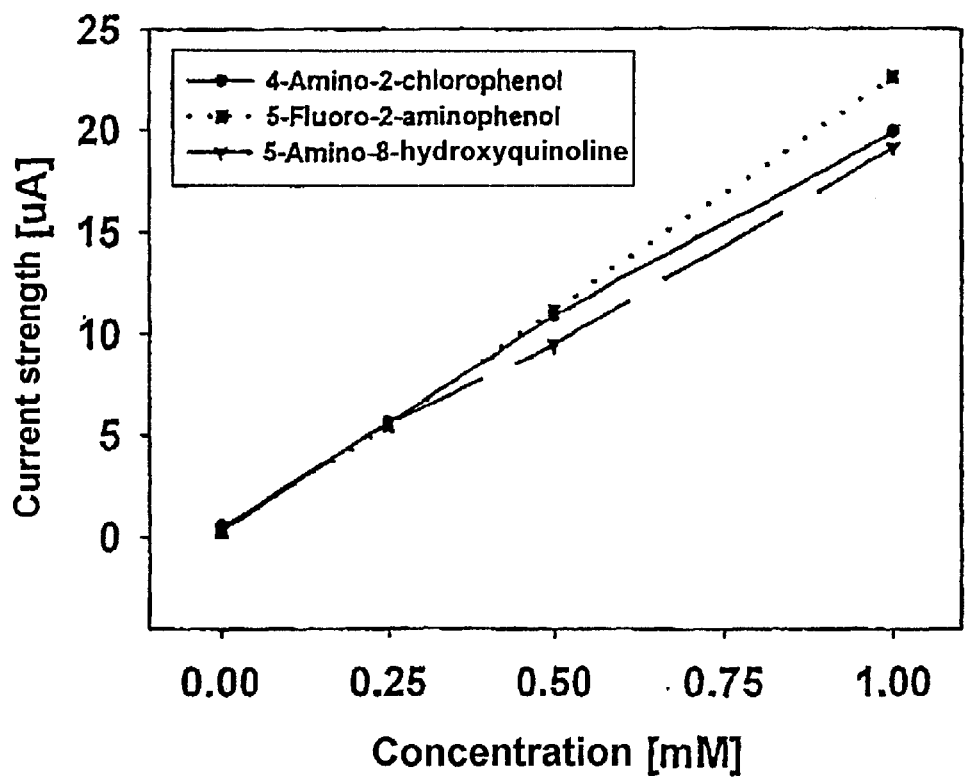
FIG. 3 the linear dependence of the current strength on the concentration of 4-amino-2-chlorophenol, 5-fluoro-2-aminophenol and 5-amino-8-hydroxyquinoline.

FIG. 3 shows the linear dependence of the current strength on the concentration of 4-amino-2-chlorophenol, 5-fluoro-2-aminophenol and 5-amino-8-hydroxyquinoline at concentrations of 0.25 mmol, 0.5 mmol and 1.0 mmol in HEPES bufffer at 300 mV by duplicate determination.

Figure 4:
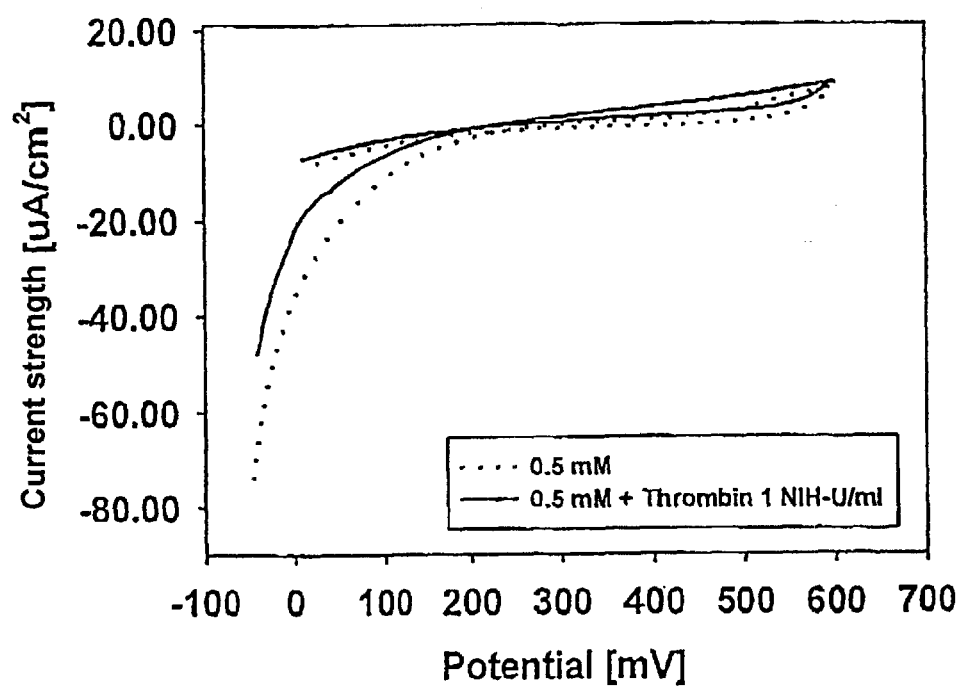
FIG. 4 a cyclic voltammigram and the hydrolysis of Tos-Gly-Pro-Arg 3-chloro-4-hydroxyanilide×AcOH.

FIG. 4 (dotted line) shows the potentiodynamic cyclic voltammigram in a measuring cell with a volume of 1 ml and an electrode surface area of 3 mm$^2$ of Tos-Gly-Pro-Arg 3-chloro-4-hydroxyanilide×ACOH at −30 to 600 mV/500 mV/m at c=0.5 mM in HEPES buffer, pH=7.4, 0.1 M KCl: the substrate advantageously shows no electroactivity at 400 mV in the equilibrium region of the electroactive compound 4-amino-2-chlorophenol, not even from the peptide part of the substrate Tos-Gly-Pro-Arg-OH. Compared with the cyclic voltammigram in the 25 ml glass beaker, the equilibrium position is reached only at 400 mV, which has no effect on the result of measurement.

FIG. 4 (full line) shows the hydrolysis of Tos-Gly-Pro-Arg 3-chloro-4-hydroxyanilide×AcOH with 1 NIH-U of thrombin and c=0.5 mM. The potentiodynamic cyclic voltammigram at 400 mV shows the substrate, the hydrolysis products Tos-Gly-Pro-Arg-OH and the electroactive species 4-amino-2-chlorophenol. There is no evident interference by the components Tos-Gly-Pro-Arg-OH or Tos-Gly-Pro-Arg 3-chloro-4-hydroxyanilide×AcOH with the electoactive species 4-amino-2-chlorophenol to be determined, so that satisfactory determination of the electroactive species 4-amino-2-chlorophenol and thus of the enzyme concentration is possible.

III. Measurement of the Enzymic Activity of Thrombin in Solution

Experimental Conditions

Thrombin 5000 NIH-U, Diagnotec Liestal 100–500

Thrombin concentration: 0.5, 1.0, 2 NIH-U/ml

Temperature: 25° C.

Buffer: HEPES buffer, 50 mM, pH 7.4, KCl, 0.1 M

Preparation

For example a 0.5 mM solution of the substrate Tos-Gly-Pro-Arg 3-chloro-4-hydroxyanilide×AcOH in HEPES buffer is prepared, as is a stock solution of thrombin with 100 NIH-U/1 ml in distilled water. 1 ml of substrate solution (c=0.5 mmol) is introduced into a 1 ml measuring cell provided with 3 electrodes of the Tacusell PGP201 potentiostat, software VM1. A cycle is allowed to run potentiodynamically from −30 to 500 mV to record the zero value (10 min). For the measurement, 10 pl of thrombin solution (final concentration 1.0 NIH-U/ml) is placed in the measuring cell, 990 μl of substrate solution are added and, after mixing for 30 sec, the current is recorded potentiostatically over a time of 10 min. The measurements are carried out as duplicate determination.

Figure 5:
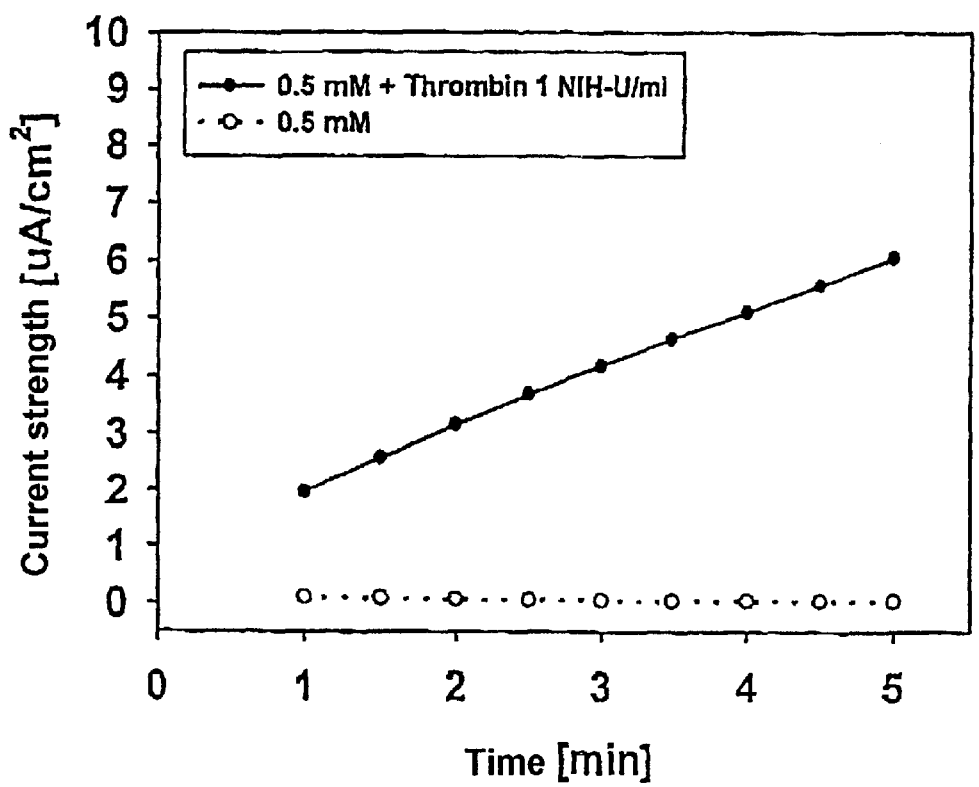
FIGS. 5–7 the linear rates of cleavage of three different substrates.
Figure 6:
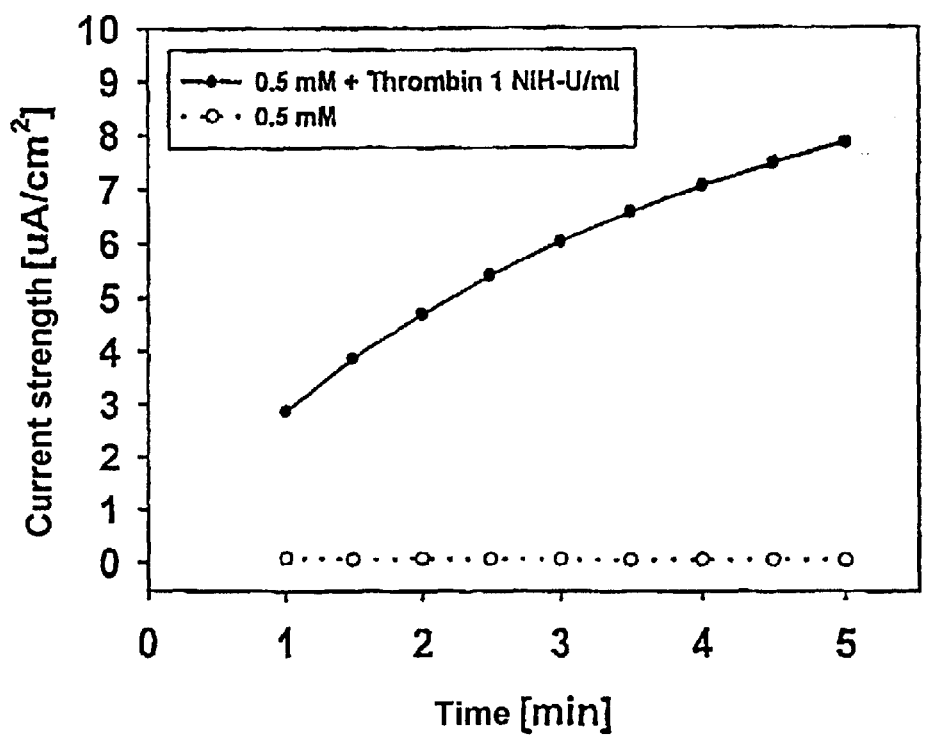
Figure 7:
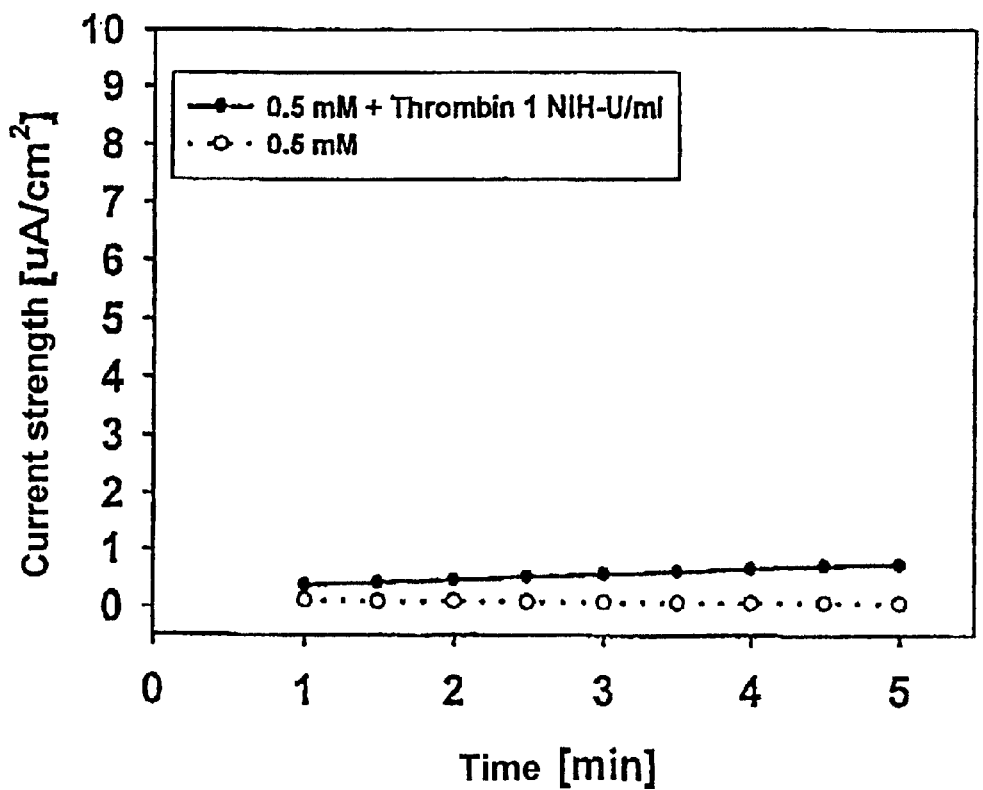

FIGS. 5, 6 and 7 ($\mu$A cm$^2$/min, T=0–5 min, at 400 mV) show the linear cleavage rates by means of 3 substrates with different electroactive groups at a thrombin concentration of 1 NIH-U and substrate concentration c=0.5 mmol:

1) Tos-Gly-Pro-Arg 3-chloro-4-hydroxyanilide×AcOH,

2) H-(D)-Chg-Gly-Arg 3-chloro-4-hydroxyanilide×2 TFA,

3) Z-Gly-Pro-Arg 2-chloro-4-hydroxyanilide×HCl.

Figure 8:
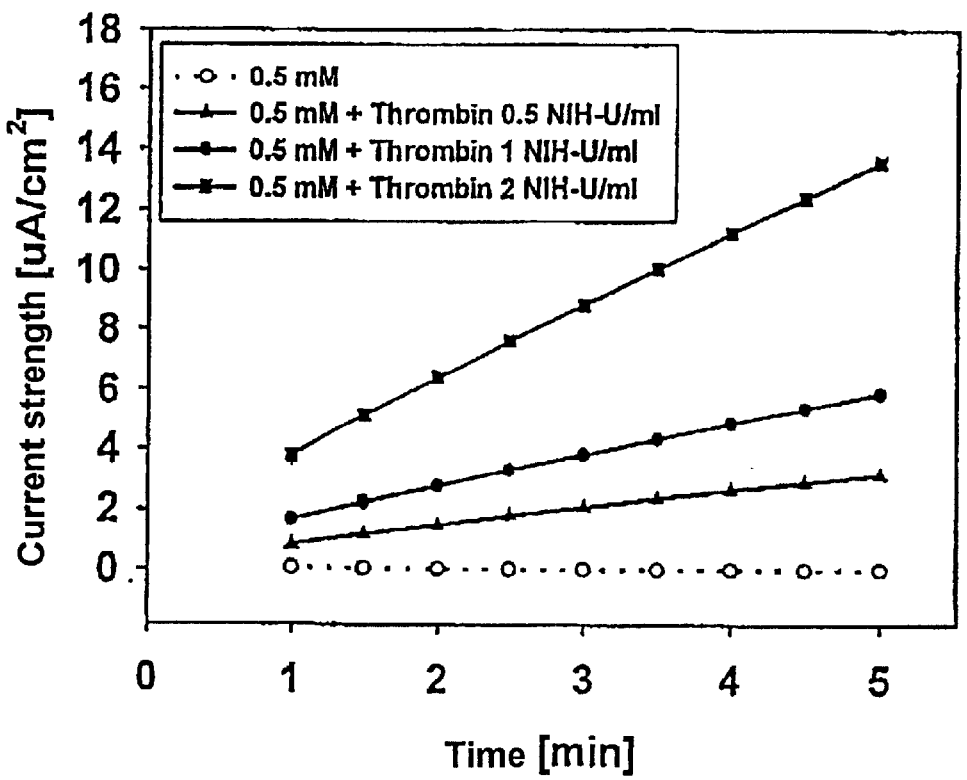
FIG. 8 the linear rates of cleavage of the substrate Tos-Gly-Pro-Arg 3-chloro-4-hydroxyanilide×AcOH with various thrombin concentrations.

FIG. 8 ($\mu$A cm$^2$/min, at 400 mV) shows the linear cleavage rates of the substrate Tos-Gly-Pro-Arg 3-chloro-4-hydroxyanilide×AcOH (c=0.5 mM) with thrombin concentrations of 0.5, 1 and 2 NIH-U (a duplicate determination was carried out).

All the examples show a satisfactory linear measurement of thrombin at various thrombin concentrations in the aqueous medium with different electroactive groups.

TABLE 1

| Substrate | Liberated electroactive species | Standardization |
|---|---|---|
| 1): Tos-Gly-Pro-Arg 3-chloro-4-hydroxy-anilide × AcOH | 4-Amino-2-chlorophenol | Hydrolysis of the substrate (c = 0.5 mmol) with 1 NIH-U of thrombin results in a current of 2 $\mu A/cm^2$ of electrode surface area in one minute |
| 2): H-(D)-Chg-Gly-Arg 3-chloro-4-hydroxy-anilide × 2 TFA | 4-Amino-2-chlorophenol | Hydrolysis of the substrate (c = 0.5 mmol) with 1 NIH-U of thrombin results in a current of 3 $\mu A/cm^2$ of electrode surface area in one minute |
| 3): Z-Gly-Pro-Arg 2-chloro-4-hydroxy-anilide × HCl | 4-Amino-3-chlorophenol | Hydrolysis of the substrate (c = 0.5 mmol) with 1 NIH-U of thrombin results in a current of 0.5 $\mu A/cm^2$ of electrode surface area in one minute |

IV. Measurement of the Enzymic Activity of Thrombin on a Metal Surface

Figure 9:
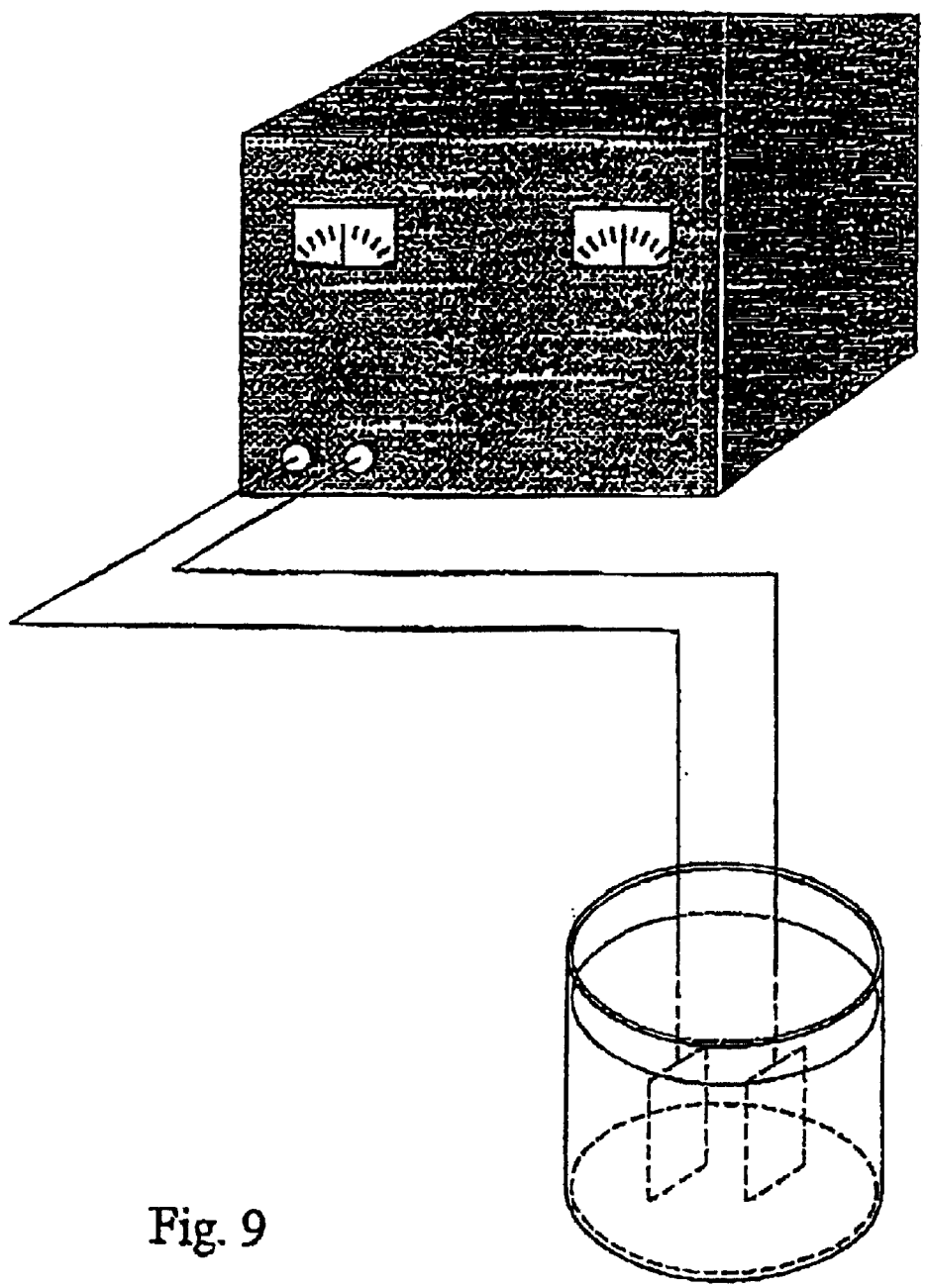
FIG. 9 diagrammatic representation of a measurement system.

FIG. 9 shows the measurement system.

A 0.5 mM substrate solution in buffer (HEPES, 50 mmol, pH 7.4, KCl 0.1 M) is placed in a 1 ml measuring cell. 2 electrodes with a metal surface (measuring electrode Pt, combined reference/auxiliary electrode Ag/AgCl) are immersed in the latter. The electrodes are connected to a potentiostat, for example Tacusell PGP201 with software VM1. (manufacturer: Radiometer). To record the zero value, a cycle is recorded potentiodynamically from −30 to 500 mV for 5 min. For the measurement, a solution of thrombin with, for example, 0.5 or 1 or 2 NIH-U is added. After 10 sec, the current is measured at a constant potential of 300 mV over a period of 5 min. The measurements are carried out as duplicate determinations.

Figure 10:
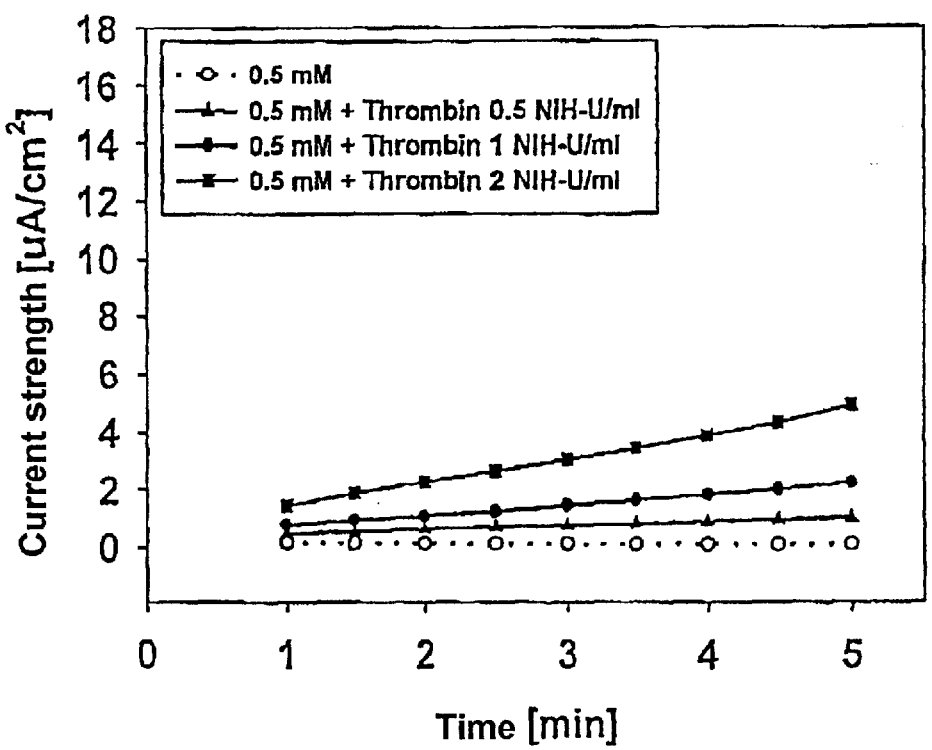
FIG. 10 another measured plot corresponding to FIG. 8 with 10 μl of thrombin at 300 mV.

FIG. 10 shows the linear cleavage rates of the substrate Tos-Gly-Pro-Arg 3-chloro-4 hydroxyanilide×AcOH ($\mu A$ $cm^2$/min, T=0–5 min, at 300 mV) with 10 $\mu l$ of thrombin with 0.5, 1 and 2 NIH-U. It is therefore possible to measure thrombin satisfactorily with the electroactive group without interference with the substrate or the peptide residue which has been cleaved off. The plot of the substrate hydrolysis agrees with the results of the substrate hydrolysis with 0.5, 1 and 2 NIH-U of thrombin in the 1 ml measuring cell.

A measurement of this type can also be carried out on a sensor strip as follows:

10 $\mu l$ of a 0.5 mM substrate solution dissolved in the abovementioned buffer are applied to a sensor strip and dried. The electrodes of the sensor are connected to a Tacussel PGP201 potentiostat, software VM 1. For the measurement, 10 $\mu l$ of a solution of thrombin with, for example 0.5 or 1 or 2 NIH-U are placed on the metal surface with adherent substrate, whereupon the substrate dissolves homogeneously. The current is followed at a constant potential of 300 mV over a period of 5 min.

This procedure is described in detail in the EP patent application by Asulab SA, Marin/Switzerland, entitled "Système électrochimique pour la détermination d'un temps de coagulationdu sang" filed on the same date.

Figure 11:
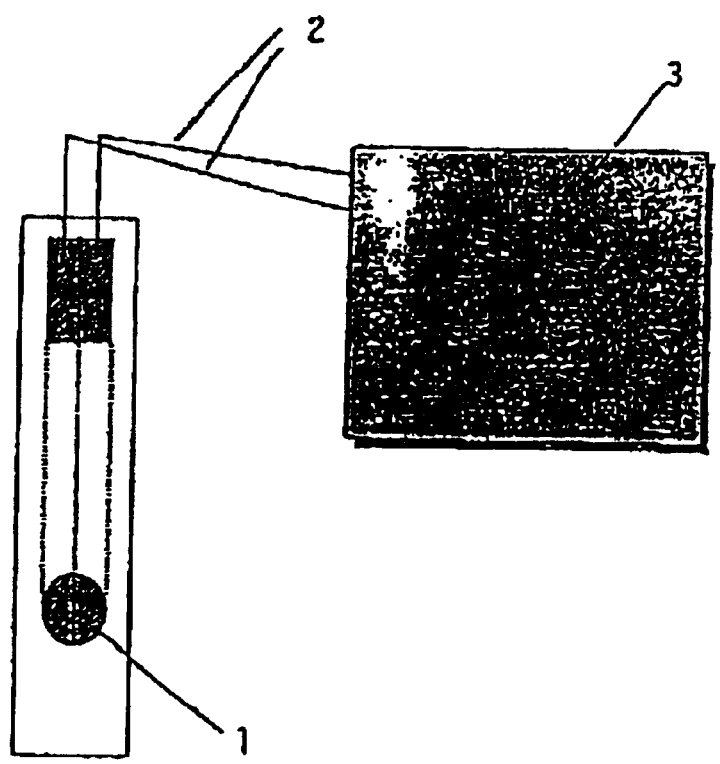
FIG. 11 diagrammatic representation of another measurement system.

V. Measurement of the Enzymic Activity of Thrombin in Whole Blood on a Metal Surface Measurement System 10 $\mu l$ of a 0.5 mmol substrate/thromboplastin solution are applied to a metal surface 1 with an area of 3.5 mm2 (FIG. 11) connected to two electrodes 2 of a Tacusell PGP201 potentiostat 3, software VM1, and dried at 30° C. for 2 h. The substrate/thromboplastin solution can be prepared, for example, in the following way: commercially available recombinant tissue factor (from American Diagnostica) was mixed with BSA solution (1 mg/ml) and diluted with HEPES, 50 mmol, pH 7.4, KCl 0.1 M. To this was added a mixture of L-α-phosphatidylcholine and L-α-phosphatidyl-L-serine dissolved in Na deoxycholate. The substrate Tos-Gly-Pro-Arg 3-chloro-4-hydroxyanilide×AcOH was added to this solution so that the substrate/thromboplastin solution contains a 0.5 mmol concentration of amperogenic substrate and 25% L-α-phosphatidylcholine (PC) and 75% L-α-phosphatidyl-L-serine (PS). The ratio of phospholipids to tissue factor is 1:10 000. For the measurement, 10 $\mu l$ of whole blood are applied to the metal surface 1 with adherent substrate/thromboplastin solution, whereupon the substrate dissolves homogeneously. After 10 sec, the current is measured at a constant potential of 500 mV over a period of 3 min. The measurements are carried out as triplicate determinations.

Figure 12:
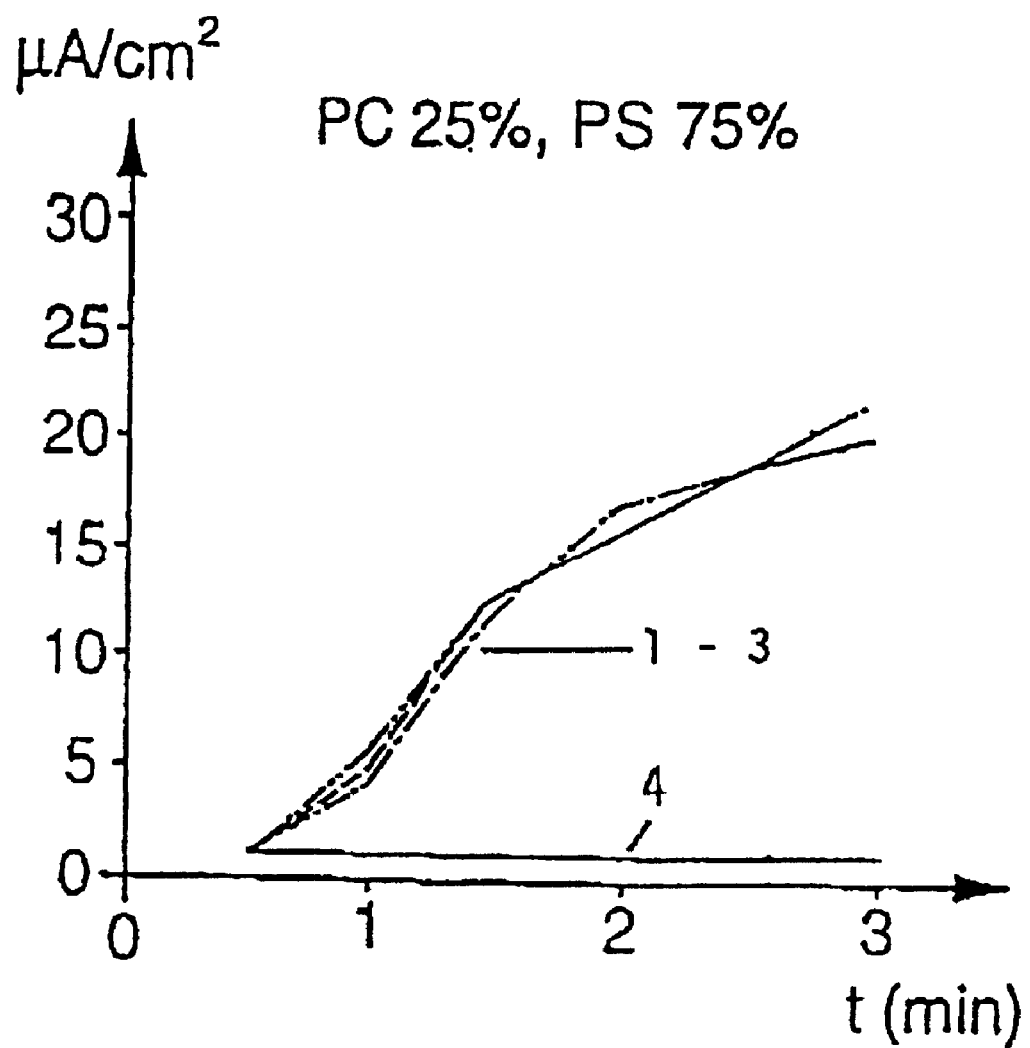
FIG. 12 further measured plots corresponding to FIG. 10 with 10 μl of whole blood at 500 mV.

FIG. 12 shows the cleavage rates of the substrate Tos-Gly-Pro-Arg 3-chloro-4-hydroxyanilide×AcOH ($\mu A$ $cm^2$/min, T=0–3 min, at 500 mV) with 10 $\mu l$ of whole blood as triplicate determination (plots 1–3 and buffer, line 4).

The following exemplary embodiments which illustrate the invention but are not intended to limit the scope thereof in any way describe the preparation of oligopeptide derivatives of the formula (I) of the invention and of salts of such oligopeptide derivatives. The eluates and products obtained according to the examples were analyzed by proton NMR, HPLC-electrospray MS or elemental analysis.

Abbreviations Used

Ala: L-alanine
Arg: L-arginine
Abu: L-2-aminobutyric acid
D-Cha: D-3-cyclohexylalanine
D-Chg: D-2-cyclohexylglycine
Gly: glycine
Pro: L-proline
AcOH: acetic acid
Boc: tert-butoxycarbonyl
t-Bups: t-butyl-phenylsulfonyl
DCH: N,N-dicyclohexylurea
DCC: dicyclohexylcarbodiimide
DMF: N,N-dimethylformamide
NHS: N-hydroxysuccinimide
HCl: hydrogen chloride
Mes: methylsulfonyl
Naps-2-: 2-naphthylsulfonyl
NMM: N-methylmorpholine
TBTU: O-(benzotriazol-1-yl)-N,N,N',N'-tetramethyluronium tetrafluoroborate
TFA: trifluoroacetic acid
Tos: p-toluenesulfonyl
Z: benzyloxycarbonyl
RT: room temperature
BSA: Bovine Albumin Serum

EXAMPLE 1
Boc-(D)-Chg-Gly-Pro-Arg 3-chloro-4-hydroxyanilide×TFA

1a: Boc-Arg 3-chloro-4-hydroxyanilide 32.1 g (98.0 mmol) of commercially available Boc-(L)-Arg-OH×HCl×H$_2$O were dissolved in 150 ml of DMF, cooled to 0° C., and 12.84 g (107.0 mmol) of isobutyl chloroformate were added. After 1 min, 10.8 g (107.0 mmol) of NMM were added. Subsequently 14.0 g (98.0 mmol) of 4-amino-2-chlorophenol were added and the solution was stirred at 0° C. for 4 h. Concentration and extraction (1-butanol/water) and purification by column chromatography (Sephadex® LH 20) resulted in 34.0 g (76.0%) of product.

| Elemental analysis: | C$_{19}$ H$_{27}$ N$_5$ O$_6$ F$_3$ Cl | | |
|---|---|---|---|
| Calc.: | C 44.41 | H 5.30 | N 13.63 |
| Found: | C 44.0 | H 5.43 | N 13.82 |

1b: H-Arg 3-chloro-4-hydroxyanilide×2 TFA 34.0 g (75.0 mmol) of 1a were stirred with 20% trifluoroacetic acid/dichloromethane at RT for 3 h. Concentration and purified by column chromatography (Sephadex® LH 20) resulted in 31.1 g (76.0%) of product.

1c: Boc-(D)-Chg-Gly-OH 8.1 g (31.5 mmol) of Boc-(D)-Chg-OH were dissolved in 100 ml of 1,2-dimethoxyethane and then, at 0° C., NHS (3.7 g, 32.0 mmol) and DCC (7.0 g, 34.0 mmol) were added. After 6 h at RT, DCH was filtered off, and a solution of 2.3 g (31.0 mml) of glycine and 2.6 g (31.0 mmol) of NaHCO$_3$ in 350 ml of water was added to the filtrate. Stirring at RT for 24 h was followed by concentration and extraction with 5% citric acid/ethyl acetate. Concentration of the organic phase resulted in 8.2 g (85.0%) of product.

1d: Boc-(D)-Chg-Gly-Pro-Arg 3-chloro-4-hydroxyanilide×TFA 4.0 g (12.7 mmol) of 1c were dissolved in 50 ml of DMF, and then 4.2 g (13.0 mmol) of TBTU and 3.9 g (39.0 mmol) of NMM were added. 6.9 g (12.7 mmol) of 1b were added to the clear solution. After 5 h at RT, the mixture was concentrated and extracted with n-butanol/water. Concentration of the organic phase and purified by column chromatography (Sephadex® LH 20) resulted in 7.0 g (68.0%) of product.

EXAMPLE 2
H-(D)-Chg-Gly-Pro-Arg 3-chloro-4-hydroxyanilide×2 TFA 6.8 g (8.4 mmol) of 1d were stirred in 20% trifluoroacetic acid/dichloromethane at RT for 3 h. Concentration and purification by column chromatography (Sephadex® LH 20) resulted in 5.0 g (72.0%) of product.

EXAMPLE 3
t-Bups-(D)-Chg-Gly-Pro-Arg 3-chloro-4-hydroxyanilide×TFA 1.2 g (1.46 mmol) of 2 were dissolved in 20 ml of DMF, and then 0.339 g (1.46 mol) of t-butylbenzenesulfonyl chloride and 0.332 g (2.92 mmol) of NMM were added. Stirring at RT for 20 h was followed by concentration, and purification by column chromatography (Sephadex® LH 20) resulted in 1.1 g (83.0%) of product.

It is also possible to use in place of t-butylphenylsulfonyl chloride as acylating agent for example the corresponding quantities of tosyl chloride, acetyl chloride, butyl chloride, octanoyl chloride, benzoyl chloride, p-methylbenzoyl chloride, 2-chlorobenzoyl chloride, methylsulfonyl chloride, n-butylsulfonyl chloride, t-butylsulfonyl chloride, isopropylsulfonyl chloride, phenylsulfonyl chloride, 1- or 2-naphthylsulfonyl chloride, (+)- or (−)-camphorsulfonyl chloride or malonyl chloride, resulting in correspondingly acylated derivatives of 2.

EXAMPLE 4
t-Bups-(D)-Chg-Gly-Pro-Arg 3-chloro-4-hydroxyanilide×AcOH 0.47 g (0.52 mmol) of 3 were dissolved in a 6:4 methanol/water solvent mixture and put onto an ion exchanger column (acetate form) and then eluted. The eluate was concentrated, and purification by column chromatography (Sephadex® LH 20) resulted in 0.388 g (88.0%) of product.

The substrate can also be protonized with a mineral acid, for example HCl, HBr, H$_2$SO$_4$ or H$_3$PO$_4$, or with an organic acid, for example formic acid, oxalic acid or tartaric acid, resulting in corresponding salts of 3.

EXAMPLE 5
Tos-Gly-Pro-Arg 3-chloro-4-hydroxyanilide×AcOH 1.8 g (5.5 mmol) of Tos-Gly-Pro-OH were activated with 1.94 g (6.0 mmol) of TBTU and 1.8 g (18 mmol) of NMM and reacted with 2.38 g (5.5 mmol) of 1b as in example 1d. The resulting Tos-Gly-Pro-Arg 3-chloro-4-hydroxyanilide×TFA (3.6 g, 4.90 mmol, 90%) was converted into the acetate salt on an ion exchanger as in example 4, yield 2.9 g, (90.0%).

| Elemental analysis: | C$_{28}$ H$_{38}$ N$_7$ O$_8$ F$_3$ Cl | | |
|---|---|---|---|
| Calc.: | C 50.33 | H 5.73 | N 14.67 |
| Found: | C 48.76 | H 5.85 | N 14.26 |

EXAMPLE 6
Z-Gly-Pro-Arg 8-hydroxyquinolin-5-ylamide×HCl 1.0 g (2.0 mmol) of Z-Gly-Pro-Arg-OH×HCl was activated with 0.2 g (2.1 mmol) of isobutyl chloroformate and 0.466 g (4.0 mmol) of NMM and reacted with 0.466 g (2.0 mmol) of 5-amino-8-hydroxyquinoline×2 HCl in analogy to example 1a to give 1.12 g (72.0%) of product.

EXAMPLE 7
Z-gly-pro-arg 2-chloro-4-hydroxyanilide×HCl 1.0 g (2.0 mmol) of Z-Gly-Pro-Arg-OH×HCl was activated with 0.2 g (2.1 mmol) of isobutyl chloroformate and 0.466 g (4.0 mmol) of nmm and reacted with 0.36 g (2.0 mmol) of 4-amino-3-chlorophenol×HCl in analogy to example 1a to give 0.875 g (70.0%) of product.

What is claimed is:

1. A compound which is an oligopeptide derivative of the formula (I) or a salt thereof $$R^1\text{—(D,L),D or}$$

$$L\text{—NH—CH(R}^2\text{)—C(=O)—N(R}^{3'}\text{)—CH(R}^3\text{)—C(=O)—Arg—R}^4$$

in which

R$^1$ is
(a) a hydrogen atom, a C$_{2-8}$-alkanoyl group optionally having an amino group in the ω position, a phenyl-C$_{2-4}$-alkanoyl group whose phenyl radical is optionally substituted in the p position by an amino group; or (b) a cyclohexylcarbonyl group which is optionally substituted in the 4 position by an aminomethyl radical, a benzoyl group which is optionally substituted in the o or p position by methyl, amino or halogen, a $C_{1-8}$-alkoxycarbonyl group, a benzyloxycarbonyl group which is optionally substituted in the p position by methoxy, methyl or chlorine; or (c) a radical of the formula —$SO_2$—$R^5$ where $R^5$ can be a $C_{1-6}$-alkyl radical, an optionally substituted aryl or heteroaryl radical or a radical of a bicyclic terpene derivative; or (d) a group of the formula —CO—CH($R^6$)—NH—$R^7$, where $R^6$ is hydrogen, a $C_{1-6}$-alkyl radical, a 1- or 2-hydroxyethyl radical, a methylmercaptoethyl radical, an aminobutyl radical, a guanidinopropyl radical, a carboxy-$C_{1-4}$-alkyl radical, a carboxamido-$C_{1-4}$-alkyl radical, a phenyl-$C_{1-4}$-alkyl radical whose phenyl radical is optionally substituted by OH, halogen, $C_{1-4}$-alkyl or methoxy, or a cyclohexyl or cyclohexylmethyl radical whose ring is option-ally substituted by OH, halogen, $C_{1-4}$-alkyl or methoxy, or a nitrogen-containing heteroaryl-$C_{1-4}$-alkyl radical with 3 to 8 carbon atoms in the heterocyclic system, where the group —CO—CH($R^6$)—NH—$R^7$ may be racemic or have the D or L configuration, and $R^7$ can be a group of type (a), (b) or (c); or (e) a group of the formula

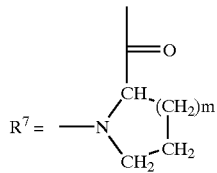

wherein m can be 1 or 2, and one of the methylene groups can be substituted by hydroxyl, carboxyl, $C_{1-4}$-alkyl or aryl-$C_{1-4}$-alkyl;

$R^2$ is hydrogen, $C_{1-6}$-alkyl, $C_{1-2}$-hydroxyalkyl, $C_{1-4}$-alkoxy-$C_{1-6}$-alkyl, benzyloxy-$C_{1-2}$-alkyl, an ω-carboxy-$C_{1-3}$-alkyl radical, an ω-$C_{1-4}$-alkoxycarbonyl-$C_{1-3}$-alkyl radical, an ω-benzyloxycarbonyl-$C_{1-3}$-alkyl radical or a cyclohexyl, cyclohexylmethyl, 4-hydroxycyclohexylmethyl, phenyl, benzyl, 4-hydroxybenzyl or imidazolyl-4-methyl radical;

$R^3$ is
(a) hydrogen or $C_{1-4}$-alkyl and $R^3$ is hydrogen; or
(b) together with $R^3$ a tri- or tetramethylene group, where one of the methylene groups can be substituted by hydroxyl, carboxyl, $C_{1-4}$-alkyl or aryl-$C_{1-4}$-alkyl; and $R^4$ is
(a) an aniline residue of the formula

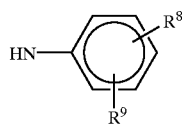

where $R^8$ can be hydroxyl and $R^9$ can be hydrogen, halogen, amino, $C_{1-4}$-alkyl, $C_{1-4}$-alkoxy or $C_{1-4}$-alkanoyl; or (b) a quinoline residue of the formula

where one of $R^{10}$, $R^{11}$ and $R^{12}$ is an —NH group via which the quinoline residue is linked to the Arg residue, another can be hydroxyl or amino, and the other can be hydrogen, hydroxyl or amino.

2. A compound of claim 1, wherein $R^5$ is methyl, isopropyl, phenyl, tert-butylphenyl, 4-methylphenyl, 2,4,6-trimethylphenyl, 2,4,6-triisopropylphenyl, 4-methoxy-2,3,6-trimethylphenyl, anthraquinoyl, 1- or 2-naphthyl, quinolyl or iso-quinolyl or a radical derived from camphor, or $R^6$, if representing a nitrogen-containing heteroaryl-$C_{1-4}$-alkyl radical with 3 to 8 carbon atoms in the heterocyclic system, is imidazolylmethyl or indolylmethyl and/or in which $R^8$ is hydroxyl in the o or p position and $R^9$ is halogen in the m position or $R^8$ is hydroxyl in the o, m or p position and $R^9$ is $C_{1-4}$-alkanoyl in the m or p position.

3. A compound of claim 1, wherein the N-terminal amino acid has a protective group selected from tert-butoxycarbonyl ("Boc"), p-toluenesulfonyl ("Tos"), tert-butylphenyl-sulfonyl ("t-Bups"), methylsulfonyl ("Mes"), naphthylsulfonyl ("Naps"), benzoyl ("Bzo"), benzyloxycarbonyl ("Z"), isopropylsulfonyl and camphorsulfonyl.

4. A compound of claim 1, wherein, apart from the C-terminal amino acid L-arginine, the compound comprises 2-aminobutyric acid, alanine, 3-cyclohexylalanine, 2-cyclohexylglycine, phenylalanine, pipecolic acid, proline or valine, it being possible for these amino acids to be in the L, D or DL form, or glycine.

5. A compound of claim 4, wherein, apart from the C-terminal amino acid L-arginine, the compound comprises L-alanine ("Ala"), L-2-amino-butyric acid ("Abu"), D-3-cyclohexylalanine ("D-Cha"), D-2-cyclohexylglycine ("D-Chg"), Glycine ("Gly") or L-proline ("Pro").

6. A compound of claim 1, in which $R^4$ is derived from 2,4-diaminophenol, 4-amino-m-cresol, 2-amino-4-chlorophenol, 4-amino-2-chlorophenol, 4-amino-3-chlorophenol, 4-fluoro-2-aminophenol, 2-fluoro-4-aminophenol, 5-fluoro-2-aminophenol, 5-amino-8-hydroxyquinoline or 2-amino-8-hydroxyquinoline.

7. A compound according to claim 1, wherein said compound is H-(D)-Chg-Gly-Arg 3-chloro-4-hydroxyanilide; Boc-(D)-Chg-Gly-Arg 3-chloro-4-hydroxyanilide; Tos-(D)-Chg-Gly-Arg 3-chloro-4-hydroxyanilide; t-Bups-(D)-Chg-Gly-Arg 3-chloro-4-hydroxyanilide; Mes-(D)-Chg-Gly-Arg 3-chloro-4-hydroxyanilide; Naps-2-(D)-Chg-Gly-Arg 3-chloro-4-hydroxyanilide; Z-(D)-Chg-Gly-Arg 3-chloro-4-hydroxyanilide; H-(D)-Cha-Gly-Arg 3-chloro-4-hydroxyanilide; Boc-(D)-Cha-Gly-Arg 3-chloro-4-hydroxyanilide; H-Gly-Pro-Arg 3-chloro-4-hydroxyanilide; Boc-Gly-Pro-Arg 3-chloro-4-hydroxyanilide; Tos-Gly-Pro-Arg 3-chloro-4-hydroxyanilide; t-Bups-Gly-Pro-Arg 3-chloro-4-hydroxyanilide; Mes-Gly-Pro-Arg 3-chloro4-hydroxyanilide; isopropylsulfonyl-Gly-Pro-Arg 3-chloro-4-hydroxyanilide; Naps-2-Gly-Pro-Arg 3-chloro-4-hydroxyanilide; (−)-camphorsulfonyl-Gly-Pro-Arg 3-chloro-4-hydroxyanilide; H-(D)-Cha-Pro-Arg 3-chloro-4-hydroxyanilide; Boc-(D)-Cha-Pro-Arg 3-chloro-4-hydroxyanilide; H-(D)-Cha-Ala-Arg 3-chloro-4-hydroxyanilide; Boc-(D)-Cha-Ala-Arg 3-chloro-4-hydroxyanilide; Boc-(D)-Cha-Abu-Arg 3-chloro-4-hydroxyanilide; Z-Gly-Pro-Arg 2-chloro-4-hydroxyanilide;

Z-Gly-Pro-Arg 5-chloro-2-hydroxyanilide; Z-Gly-Pro-Arg 8-hydroxyquinolin-5-ylamide; Boc-(D)-Chg-Gly-Pro-Arg 3-chloro-4-hydroxyanilide; H-(D)-Chg-Gly-Pro-Arg 3-chloro4-hydroxyanilide; or t-Bups-(D)-Chg-Gly-Pro-Arg 3-chloro-4-hydroxyanilide.

8. A salt of a compound of claim 1 with HCl, HBr, $H_2SO_4$ or $H_3PO_4$ or with formic, acetic, propionic, phthalic, citric, oxalic, tartaric, benzoic, lactic, trichloroacetic or trifluoroacetic acid.

9. A salt of claim 8 with HCl, acetic acid or trifluoroacetic acid.

10. A process for preparing a compound or a salt thereof of claim 1, comprising:

linking an amine of the formula $H—R^4$ to the carboxyl group of arginine, whose amino group is protected or already has an appropriately protected residue of the peptide part of the desired product or a part thereof, and whose guanidino group is protected;

optionally assembling the peptide part of the desired product completely;

optionally cleaving off the remaining protective group(s);

optionally acylating a free amino group;

optionally converting a resulting oligopeptide derivative of the formula I into an acid addition salt; and/or converting a resulting acid addition salt of the oligopeptide derivative into a free oligopeptide derivative or into another salt.

11. A method for the quantitative determination of a protease or antiprotease, comprising;

contacting the protease or antiprotease in an aqueous or organic medium with a compound or a salt thereof of claim 1; and determining by amperometry the electroactive amine of the formula $H—R^4$, which is cleaved off by the protease or antiprotease to be determined and which can be electrochemically oxidized or reduced.

12. The method of claim 11, wherein the protease or antiprotease is of the blood coagulation system, of the fibrinolytic system or of the complement system.

13. The method of claim 11, wherein the amperometry is carried out using an apparatus having a potentiostat and a measuring cell with two or three electrodes made of steel or a noble metal, a reference electrode and/or an auxiliary electrode, to which the oligopeptide derivative or a salt thereof and optionally a water-soluble $Ca^{++}$ salt, phospholipid, and/or thromboplastin reagent are applied.

14. The method of claim 13, wherein a mixture of 0–35 mol % of L-α-phosphatidylcholine (PC) and 65–100 mol % of L-α-phosphatidyl-L-serine (PS) is used as phospholipids.

15. The method of claim 13, wherein the mixture comprises 25–35 mol % PC and 65–75 mol % PS.

16. The method of claim 13, wherein a change in the concentration of the electroactive amine in the measuring cell is determined through measuring an oxidation or reduction current.

17. The method of claim 13, wherein the protease is thrombin.

18. The method of claim 17 for determining thrombin in whole blood, wherein the whole blood is applied directly, without removal of other constituents of the blood, onto the electrode to which the oligopeptide derivative or a salt thereof and optionally a water-soluble $Ca^{++}$ salt, phospholipid, and/or thromboplastin reagent are adhering.

* * * * *